United States Patent [19]

Bonaventura et al.

[11] Patent Number: 5,334,705
[45] Date of Patent: Aug. 2, 1994

[54] BENZENETRICARBOXYLATE DERIVATIVE-CROSSLINKED LOW OXYGEN AFFINITY HEMOGLOBIN

[75] Inventors: Joseph Bonaventura; Marius Brouwer; Robert E. Cashon, all of Beaufort, N.C.

[73] Assignee: Duke University, Durham, N.C.

[21] Appl. No.: 745,637

[22] Filed: Aug. 15, 1991

[51] Int. Cl.$^5$ .................... A61K 37/00; A61K 35/14; A61K 37/02; C07K 13/00
[52] U.S. Cl. .................................... 530/385; 530/410
[58] Field of Search ...................... 514/6; 530/385, 410

[56] References Cited

U.S. PATENT DOCUMENTS

| | | | |
|---|---|---|---|
| 4,061,736 | 12/1977 | Morris et al. | 514/6 |
| 4,301,144 | 11/1981 | Iwashita et al. | 251/129.12 |
| 4,412,989 | 11/1983 | Iwashita et al. | 514/762 |
| 4,529,719 | 7/1985 | Tye | 514/6 |
| 4,584,130 | 4/1986 | Bucci et al. | 301/66 |
| 4,600,531 | 7/1986 | Walder | 514/832 |
| 4,650,786 | 3/1987 | Wong | 514/6 |
| 4,670,417 | 6/1987 | Iwasaki et al. | 514/6 |
| 4,710,488 | 12/1987 | Wong | 514/6 |

OTHER PUBLICATIONS

Walder et al., Biochemistry 18:418–426 (1979).
Snyder et al., Proc. Natl. Acad. Sci. USA 84:7280–7284 (1987).
Bucci, E. et al., J. Biol. Chem. 264:6191–6195 (1989).
Chang et al., IN: Chang, TMS et al., ed., *Blood Substitutes*, Marcel Dekker, Inc., New York, 1989, pp. 11–29.
Venuto, In: Chang, TMS et al., ed., *Blood Substitutes*, Marcel Dekker, Inc., New York, 1989, pp. 77–83.
Chang et al., In: Chang, TMS et al., ed., *Blood Substitutes*, Marcel Dekker, Inc., New York, 1989, pp. 205–215.
Matsushita et al., In: Chang, TMS et al., ed., *Blood Substitutes*, Marcel Dekker, Inc., New York, 1989, pp. 247–260.
Kavanaugh et al., In: Chang, TMS et al., ed., *Blood Substitutes*, Marcel Dekker, Inc., New York, 1989, p. 637.
Keipert et al. In: Chang, TMS et al., ed., *Blood Substitutes*, Marcel Dekker, Inc., New York, 1989, pp. 643–645.
Vandegriff et al., In: Chang, TMS et al., ed., *Blood Substitutes*, Marcel Dekker, Inc., New York, 1989, pp. 647–649.
Nishi, et al. In: Chang, TMS et al., ed., *Blood Substitutes*, Marcel Dekker, Inc., New York, 1989, pp. 653–655.
Manning et al., Proc. Natl. Acad. Sci. USA 88:3329–3333 (1991).
Hess et al., J Appl Physiol 70:1639–1644 (1991).
Przybelski et al., J Lab Clin Med 117:143–151 (1991).
Hess et al., Biomater Artif Cells Artif Organs 17:632 (1989).
Marini et al., Biomater Artif Cells Artif Organs 17:638 (1989).
MacDonald et al., FASEB J. 3:A612 (1989).
Jones et al., Biomater Artif Cells Artif Organs 17:643 (1989).
Kavanaugh et al., J. Biol. Chem. 264:11009–11013 (1989).
Shimizu et al., Biochemistry 13: 809–813 (1984).
Benesch, Biochem. Biophys. Res. Comm. 156:9–14 (1988).

(List continued on next page.)

*Primary Examiner*—Howard E. Schain
*Assistant Examiner*—P. Lynn Touzeau
*Attorney, Agent, or Firm*—Pennie & Edmonds

[57] ABSTRACT

The invention is directed to a low oxygen affinity stroma-free tetrameric mammalian hemoglobin which is produced by crosslinkng with a derivative of benzenetricarboxylate, as well as methods for its preparation. Crosslinked stroma-free hemoglobin produced by methods of the present invention may be used in applications requiring physiological oxygen carriers such as in blood substitute solutions, or as in a plasma expander.

9 Claims, 7 Drawing Sheets

OTHER PUBLICATIONS

MacDonald et al., Biomater. Artif. Cells Artif. Organs 18: 263-282 (1990).

Clifford et al., Biomater. Artif. Cells Artif. Organs 18: 321-328 (1990).

Greenburg, Biomater. Artif. Cells Artif. Organs 16: 71-75 (1988).

Sehgal et al., Surgery 95:433-438 (1984).

Shimizu and Bucci, "Allosteric Effectors of Hemoglobin. Interaction of Human Adult and Fetal Hemoglobins with Poly(carboxylic acids)", Biochemistry 13: 809-814 (1974).

Banerjee and Desbois, "Effect of polycarboxylate anions on hemoglobin", C.R. Acad. Sc. Paris 227 (Series D): 963-966 [full length French article and English translation thereof (pp. 1-7)].

BENZENETRICARBOXYLATE DERIVATIVE-CROSSLINKED LOW OXYGEN AFFINITY HEMOGLOBIN

1. FIELD OF THE INVENTION

The invention is directed to a low affinity stroma-free tetrameric mammalian hemoglobin which is crosslinked with a derivative of benzenetricarboxylate. Crosslinked stroma-free hemoglobin produced by methods of the present invention may be used in applications requiring physiological oxygen carriers such as in blood substitute solutions, or as in a plasma expander.

2. BACKGROUND OF THE INVENTION

2.1. Blood Substitutes

Transfusion of a patient with donated blood has a number of disadvantages. Firstly, there may be a shortage of a patient's blood type. Secondly, there is a danger that the donated blood may be contaminated with infectious agents such as hepatitis viruses, cytomegalovirus, Epstein-Barr virus, serum parvoviruses, syphilis, malaria, filariasis, trypanosomiasis, babsiosis, pathogenic bacteria, and HIV (Bove, 1986, Progr. Hematol. 14:123–145). Thirdly, donated blood has a limited shelf life.

An alternative to transfusion involves the use of a blood substitute. A blood substitute is an oxygen carrying solution that also provides the oncotic pressure necessary to maintain blood volume. Two types of substitutes have recently been studied, fluorocarbon emulsions and hemoglobin solutions.

Fluorocarbons however are not feasible blood substitutes, since they are known at times to block the natural immune system (Dellacherie, 1986, Crit. Rev. Ther. Drug Carriers 3: 41–94). In addition, the use of fluorocarbons is limited to situations in which high partial pressures of oxygen can be administered. They do not have a sufficiently high oxygen binding capacity for use under normal physiological conditions.

Hemoglobin as it exists within the red blood cell is composed of two alpha-like globin chains and two beta-like globin chains, each with a heme residue. One alpha-like globin chain and one beta-like globin chain combine to form a dimer which is very stable. Alpha-like and beta-like globin genes are each a family of related globin genes which are expressed at different stages of development and regulated by oxygen tension, pH, and the development from embryo to fetus to newborn. Two dimers then line up in antiparallel fashion to form tetramers. The binding of dimers to form the tetramers is not as strong as in the case of monomers binding to associate into dimers. The tetramers, therefore, have a tendency to fall apart to form dimers and there is always an equilibrium between tetramers, dimers, and monomers. At high concentrations of globin, the predominant form is the tetramer; with dilution, the dimer becomes the predominant form. This equilibrium is also affected by solvent, salts, pH and other factors as the forces binding the monomers together are primarily electrostatic.

Hemoglobin may exist under two conformations, the oxygenated (R-form) or deoxygenated (T-form). The deoxy structure is stabilized by the formation of salt bridges involving definite amino and carboxylic groups of globins.

The oxygen binding characteristics of hemoglobin can be characterized by a curve, called the oxygen affinity curve, obtained by plotting the fractions of available hemoglobin sites saturated with oxygen as a function of the partial pressure of oxygen in equilibrium with the solution. Information may be obtained from such plots regarding the cooperativity of oxygen binding to hemoglobin using the following Hill equation:

$$Y/1 - Y = K[O_2]^n$$

where Y is the fraction of sites occupied by oxygen and n is the Hill coefficient, which reflects the degree of cooperativity between subunits, and K is the association constant for the overall oxygen binding process. Therefore, the value of the Hill coefficient can be considered as a useful reflection of the efficacy of the oxygen-carrying function. The oxygen affinity of hemoglobin may also be characterized by determining the $P_{50}$, which is the partial oxygen pressure which leads to 50% saturation.

The alpha-like globin genes of hemoglobin are clustered together on chromosome 16 and include genes encoding the embryonic zeta globin chain and the adult alpha globin chain, present in both the fetus and newborn. The beta-like globin genes reside on chromosome 11 and include genes encoding the embryonic epsilon-globin chain, the fetal gamma-globin chain, and the adult delta-globin and adult beta-globin chains. Two types of gamma globin chains have been identified, $G_{gamma}$ and $A_{gamma}$, which differ by the presence of a single glycine or alanine residue, respectively, at amino acid 135 (Schroeder et al., 1968, Proc. Natl. Acad. Sci. U.S.A. 60: 537–544). The gamma chain has been found to contain a polymorphic site at position 75, which also can be occupied either by isoleucine or threonine. A variety of hemoglobins may be formed (reviewed in Kutlar et al., 1989, Hemoglobin 13:671–683 and Honig and Adams, Human Hemoglobin Genetics, Springer Verlag, New York pp. 29–33). Examples of hemoglobins (Hb) include hemoglobin A (HbA-$alpha_2beta_2$), $HbA_2$ ($alpha_2delta_2$), HbF ($alpha_2gamma_2$), Hb Barts ($gamma_4$), HbH ($beta_4$), and Hb Portland I ($zeta_2gamma_2$), Hb Portland II ($zeta_2beta_2$), Hb Portland III ($zeta_2delta_2$) Hb Gower I ($zeta_2epsilon_2$), and Hb Gower II ($alpha_2epsilon_2$).

There are obstacles however to using native hemoglobin as a blood substitute. Firstly, large dosages are required (Walder, 1988, Biotech '88, San Francisco, Nov. 14–16, 1988). A single unit (450 ml) of a 10% hemoglobin solution contains 45 g of protein. It is estimated that ten million units of blood are used in the U.S. per year. Therefore, the production of 450,000 kg of hemoglobin per year would be required. Secondly, it is important to obtain hemoglobin that is free from infectious agents and toxic substances. Thirdly, although hemoglobin is normally a tetramer of 64,000 molecular weight, it can dissociate to form alpha-beta dimers. The dimers are rapidly cleared by the kidneys and the residence time is much too short for cell-free hemoglobin to be useful as a blood substitute. Fourthly, cell-free hemoglobin has too high an oxygen affinity to effectively release oxygen to the tissues due to the absence of 2,3-diphosphoglycerate (2,3-DPG). Efforts to restore 2,3-DPG have been unsuccessful since 2,3-DPG is rapidly eliminated from the circulation.

2.2. Chemical Modification of Hemoglobin

One approach that has been taken to circumvent the problem of dissociation of the hemoglobin tetramet to a dimer has been to chemically modify the hemoglobin by either intramolecular or intermolecular crosslinking. Examples of such modification include crosslinking with polyalkylene glycol (Iwashita, U.S. Pat. Nos. 4,412,989 and 4,301,144), with polyalkylene oxide (Iwasake, U.S. Pat. No. 4,670,417); with a polysaccharide (Nicolau, U.S. Pat. Nos. 4,321,259 and 4,473,563); with inositol phosphate (Wong, U.S. Pat. Nos. 4,710,488 and 4,650,786); with a bifunctional crosslinking agent (Morris et al., U.S. Pat. No. 4,061,736); with insulin (Ajisaka, U.S. Pat. No. 4,377,512); with a dialdehyde (Bonhard et al., U.S. Pat. No. 4,777,444); and with a crosslinking agent so that the hemoglobin composition is intramolecularly crosslinked between lys 99 alpha$_1$ and lys 99 alpha$_2$ (Walder, U.S. Pat. No. 4,598,064).

Another approach has involved the polymerization of hemoglobin to produce a polyhemoglobin. Polyhemoglobin has been found to have a longer circulation in blood than a hemoglobin tetramet. Polyhemoglobins have been obtained by crosslinking hemoglobin with glutaraldehyde (PCT Application Publication No. WO 88/03408; and Keipert et al., 1982, Int. J. Art. Org. 5:383–385).

Hemoglobin has also been chemically modified to decrease the oxygen affinity of isolated hemoglobin. One approach has involved polymerization with pyridoxal phosphate (Sehgal et al., 1984, Surgery, 95:433–438). A variation of the approach involving polymerization with pyridoxal phosphate has also been disclosed and comprises reacting the hemoglobin with a stabilizing agent and then subsequently reacting the stabilized hemoglobin with pyridoxal phosphate (European Patent Application Publication No. 361,720, published Apr. 4, 1990; Tye, U.S. Pat. No. 4,529,719; and Maffuid et al., 1983, Surg. Forum 34:5–7). Another approach has involved the use of reagents that mimic 2,3-DPG (Bucci et al., U.S. Pat. No. 4,584,130; and Shimizu and Bucci, 1974, Biochemistry 13:809–813). Although these compounds do lower the oxygen affinity of hemoglobin, the affinity is still relatively high.

In another approach, hemoglobin has been crosslinked intramolecularly with periodate-oxidized ATP (o-ATP) and intermolecularly with periodate-oxidized adenosine (o-adenosine), and combined with reduced glutathione (GSH) (PCT Application Publication No. WO 91/09615).

3. SUMMARY OF THE INVENTION

The invention is directed to a stroma-free tetrameric mammalian hemoglobin having an affinity for oxygen which is lower than that of non-crosslinked hemoglobin A, and which is crosslinked with a crosslinking agent derived from a benzenetricarboxylate. In a preferred embodiment, the stroma-free hemoglobin is crosslinked with a crosslinking agent having the formula in which R is a diaspirin moiety having the structure in which $X_1$ and $X_2$ are selected from —H, —Br, I, —NO$_2$. Crosslinked stroma-free hemoglobin produced by methods of the present invention may be used in applications requiring physiological hemoglobin-based oxygen carriers such as in blood substitute solutions, or as in a plasma expander.

3.1. Definitions
Bis-tris:bis(2-hydroxyethyl)iminotris-(hydroxymethyl)methane
BTC:benzenetricarboxylate
Hb:hemoglobin
IHP:inositol hexaphosphate
Ret. Time:retention time
SDS:sodium dodecyl sulfate
TLC:thin layer chromatography
Tris:tris(hydroxymethyl)aminomethane

5. DETAILED DESCRIPTION OF THE INVENTION

The invention is directed to a stroma-free tetrameric mammalian hemoglobin having an affinity for oxygen which is lower than that of non-crosslinked hemoglobin A, and which is produced by a method comprising crosslinking with a benzenetricarboxylate derivative. In a most specific embodiment, the benzenetricarboxylate derivative is bis 1,3 di- (3,5-dibromosalicyl) benzenetricarboxylate. The mammalian hemoglobin may be for example, any human hemoglobin, including but not limited to HbA (alpha$_2$beta$_2$), HbA$_2$ (alpha$_2$delta$_2$), HbF (alpha$_2$gamma$_2$), Hb Barts (gamma$_4$), HbH (beta$_4$), and Hb Portland I (zeta$_2$gamma$_2$), Hb Portland II (zeta$_2$beta$_2$), Hb Portland III (zeta$_2$delta$_2$) Hb Gower I (zeta$_2$epsilon$_2$), and Hb Gower II (alpha$_2$epsilon$_2$); as well as any other animal hemoglobin, e.g. bovine or porcine hemoglobin. The benzenetricarboxylate-crosslinked hemoglobin may be used in applications requiring physiological oxygen carriers such as in blood substitute solutions, or as in a plasma expander.

5.1. Preparation of Benzenetricarboxylate Derivative-Crosslinked Low Oxygen Affinity Hemoglobin Three steps are involved in the preparation of a stroma-free tetrameric mammalian hemoglobin having an affinity for oxygen which is lower than that of non-crosslinked hemoglobin A, and which is produced by crosslinking with a benzenetricarboxylate derivative:
(a) obtaining a composition comprising hemoglobin;
(b) crosslinking the isolated hemoglobin with a benzenetricarboxylate derivative; and
(c) recovering the crosslinked hemoglobin.

5.1.1. Obtaining Hemoglobin

The starting material, unmodified hemoglobin may be obtained using procedures known in the art (see for example PCT Application Publication No. WO 88/03408, published May 19, 1988; U.S. Pat. No. 4,001,401; Feola et al., 1983, Surgery Gynecology and Obstetrics 157:399–408; De Venuto et al., 1979, Surgery Gynecology and Obstetrics 149:417–436). For example, unmodified stroma-free hemoglobin may be obtained as follows: (a) obtaining whole blood; (b) separating red blood cells from other components of whole blood; (c) isolating the hemoglobin from the erythrocytes; and (d) separating the hemoglobin from stroma and other impurities.

Stroma-free hemoglobin can be prepared starting with erythrocytes in freshly drawn, outdated, or frozen packed cells or whole blood. The blood should be drawn in a sterile fashion into containers with sufficient anticoagulant activity to prevent clot formation.

In one embodiment, the erythrocytes are washed in a saline solution and centrifuged to separate red blood cells from white blood cells and to additionally remove free proteins (Feola et al., 1983, Surgery Gynecology and Obstetrics 157:399–408). In another embodiment, the red cells may be separated from other erythrocytes by passing through a semi-continuous type centrifuge as described in PCT Application Publication No. WO 88/03408, published May 19, 1988.

Hemoglobin may be isolated in one embodiment by diluting the red blood cell solution in water or an organic solvent at 2°–10° C. to separate the hemoglobin in red blood cells from all cell debris (PCT Application Publication No. WO 88/03408, published May 19, 1988; U.S. Pat. No. 4,001,401; Feola et al., 1983, Surgery Gynecology and Obstetrics 157:399–408). In another embodiment, the hemoglobin is precipitated as a zinc complex by the addition of a zinc salt to a hemoglobin solution (De Venuto et al., 1979, Surgery Gynecology and Obstetrics 149:417–436).

The isolated hemoglobin may in one embodiment be purified by ultrafiltration through for example a 0.5 filter which retains the cellular components and passes the hemoglobin.

Hemoglobin may also be obtained through other procedures known in the art. For example, bacterial strains (see for example Nagai and Hoffman, U.S. Pat. No. 5,028,588, issued Jul. 2, 1991) or yeast (see for example PCT Application Publication No. WO 90/13645, published Nov. 15, 1990), or other eukaryotic organisms may be engineered to produce hemoglobin by recombinant DNA techniques.

5.1.2. Crosslinking the Isolated Hemoglobin with a Benzenetricarboxylate Derivative In a preferred embodiment, the hemoglobin is deoxygenated. Deoxygenation may be accomplished by extensively treating the hemoglobin prior to cross-linking with inert gases such as nitrogen, argon, or other inert gases. Alternatively, or in combination with inert gases, deoxygenation may be achieved by treating the hemoglobin with dithionite or other conventional reducing agents, such as ferrous citrate.

The deoxygenated hemoglobin is subsequently crosslinked with a benzenetricarboxylate derivative which is reactive with protein lysine amino groups. In one embodiment, the crosslinking agent is an acid chloride of benzenetricarboxylate. In a preferred embodiment, the crosslinking agent has the formula in which R is a diaspirin moiety having the structure in which $X_1$ and $X_2$ are selected from —H, —Br, I, —NO$_2$. In a most preferred embodiment, the crosslinking agent is bis 1,3 di- (3,5-dibromosalicyl) benzenetricarboxylate.

The reaction of hemoglobin with the crosslinking agent derived from benzenetricarboxylate can occur at a temperature of from about 15° C. to about 25° C., preferably from about 18° C. to about 22° C. The pH of the reaction can vary from about 7 to about 9, preferably from about 8.0 to about 8.5, typically having an ionic strength of 25 molar Tris buffer in a molar salt solution up to a concentration of about 50 molar. The ratio of hemoglobin to the crosslinking agent (the benzenetricarboxylate derivative) can be from about 1:2 to about 1:10, preferably 1:5. The time for the reaction will vary, but can be up to 18 hrs. for a sufficient crosslinking of hemoglobin to have occurred.

5.1.3. Purification of Low Oxygen Affinity Benzenetricarboxylate-Crosslinked Hemoglobin The low oxygen affinity of the benzenetricarboxylate derivative-crosslinked hemoglobin may be isolated and purified using standard methods known in the art including but not limited to chromatography (e.g., ion exchange, affinity, and sizing column chromatography), centrifugation, differential solubility, or by any other standard technique for the purification of proteins. The chromatographic procedure employed may for example be high pressure liquid chromatography, fast pressure liquid chromatography, or ordinary column chromatography.

The oxygen affinity of the various fractions obtained from the separation procedures described above may be determined using procedures known in the art, e.g. determining the $P_{50}$. Methods for determining the $P_{50}$ include but are not limited to tonometry, where bound oxygen is measured by changes in the optical spectrum of the oxygen carrier (reviewed in Gill, Methods in Enzymology vol. 76, E. Antonini, L. Rossi-Bernardi, and E. Chancone, eds., Academic Press, NY (1981), pp. 427–439); a thin layer optical method where a thin layer of hemoglobin solution is exposed to oxygen at various partial pressures, while the oxygen saturation of the sample is monitored spectrophotometrically (reviewed in Gill, in Methods in Enzymology vol. 76, E. Antonini, L. Rossi-Bernardi, and E. Chancone, eds., Academic Press, NY (1981), pp. 427–438 and Lapennas et al., in Methods in Enzymology vol 76, E. Antonini, L. Rossi-Bernardi, and E. Chancone, eds., Academic Press, NY (1981), pp. 449–469); and a dynamic method where the partial pressure of oxygen, p, is changed continuously but slowly enough to maintain the equilibrium at any moment, and p and the fractional oxygen saturation of hemoglobin, Y are determined and recorded continuously (reviewed in Imai, in Methods in Enzymology vol. 76, E. Antonini, L. Rossi-Bernardi, and E. Chancone, eds., Academic Press, N.Y. (1981), pp. 438–449).

In a preferred embodiment, the $P_{50}$ of the isolated benzenetricarboxylate derivative-crosslinked hemoglobin is at least twice as high as hemoglobin A when measured under substantially the same conditions. The $P_{50}$ is defined as the partial pressure of $O_2$ required to cause 50% saturation of $O_2$ binding sites.

5.2. Uses for Activated Benzenetricarboxylate Derivative-Crosslinked Low Oxygen Affinity Hemoglobin The hemoglobin compositions of the present invention may be used as blood substitutes or as a blood plasma expander, in a pharmaceutical composition with an acceptable carrier, and with other plasma expanders, or in any application where a physiological oxygen carrier is needed. The pharmaceutical carriers may be such physiologically compatible buffers as Hank's or Ringer's solution, physiological saline, a mixture consisting of saline and glucose, and heparinized sodium-citrate-citrate acid-dextrose solution. The hemoglobin produced by the methods of the present invention can be mixed with colloidal-like plasma substitutes and plasma expanders such as linear polysaccharides (e.g. dextran, hydroxyethyl starch, balanced fluid gelatin, and other plasma proteins). Additionally, the hemoglobin may be mixed with water soluble, physiologically acceptable, polymeric plasma substitutes, examples of which include polyvinyl alcohol, poly(ethylene oxide), polyvinylpyrrolidone, and ethylene oxide-polypropylene glycol condensates. Techniques and formulations for administering the compositions comprising the hemoglobin generally may be found in *Remington's Pharmaceutical Sciences*, Meade Publishing Col., Easton, Pa., latest edition.

The following examples are presented by way of illustration not by way of limitation.

6. Example: Benzenetricarboxylic Acid (BTC) Crosslinked Hemoglobin

In the Example described herein, human HbA is crosslinked using a diaspirin type crosslink with 1,3,5-benzenetricarboxylic acid (BTC) as the crosslinking group. Oxygen binding studies in the presence and absence of the strong allosteric effector, inositol hexaphosphate indicate that the crosslinking group blocks the beta-chain anionic binding site. Functional studies show that the crosslinking induces a high degree of asymmetry into the binding curve with a decrease in cooperativity and a shift to lower oxygen affinity of at least a portion of the binding sites on the tetramer.

6.1. Preparation of Bis 1,3 Di-(3,5-Dibromosalicylic) BTC 5.5 gm of 2,3-dibromosalicylic acid (DBS) was added to 70 ml of toluene and 14 ml of N,N-dimethylaniline (DMA) in a stirred round bottom flask forming a thin slurry. Ethyl acetate (approximately 20 ml) was added slowly dropwise until the solution cleared, indicating that the DBS has gone into solution. 1.65 gm of benzenetricarboxylic acid dissolved in 5 ml toluene is added to the reaction mixture. At this point, the reaction mixture turned bright red-orange. Within 5 minutes a dark viscous oil precipitate began to form. During this time, the solution begins to turn yellow-green. The reaction flask was stirred for 1 hour. At this point, thin layer chromatography (TLC) of the solution shows a significant amount of DBS still in solution. Another 0.5 gm of BTC was added to the reaction mixture. On addition of this BTC, the solution again goes to yellow-orange then slowly back to green. Another 0.5 gm addition of BTC increases the amount of gooey precipitate in the flask. The reaction mixture is allowed to stir overnight.

The next morning, the green solution phase is decanted from the precipitate, extracted with cold-acidified water, dried over anhydrous sodium sulfate ($Na_2SO_4$) and set aside for the solvent to evaporate. The precipitate is dissolved in a minimum volume of methanol. Reprecipitation of the methanolic precipitate solution by adding a large volume of distilled water yields a greenish powder which appears to be enriched for the substance visible under short-wave UV. A second reprecipitation yields a lighter blue colored powder.

6.2. Preparation of Hemoglobin from Whole Blood

The following procedure was used in the preparation of hemoglobin from outdated whole blood. The procedure was generally carried out at 0° C. The blood was centrifuged at 2000 g for five minutes. The supernatant was drawn off by aspiration, using a Pasteur pipette.

The red blood cells were washed three times with 5–10 volumes of 0.8% sodium chloride. The cells were lysed with four volumes of cold deionized water, stirred with a glass rod or vortexed, during the addition of the water. After lysis, the hemolysate was gently stirred in a beaker or flask immersed on crushed ice for fifteen minutes. Unlysed cells and stroma were removed by high speed centrifugation. Subsequently, 0.2 volumes of saturated ammonium sulphate to the clear supernatant (saturated at 4° C.).

After allowing hemoglobin to stand for 10 minutes with no stirring, the solution was centrifuged at 27,000 g in the SS-34 rotor of a Sorvall centrifuge for 30 minutes. The hemolysate (supernatant) was dialyzed versus 2–3 changes of cold deionized water for +24 hours (50 volumes excess of water over hemolysate).

The dialyzed hemolysate was centrifuged at 27,000 g on the SS-34 rotor rotor, for 10 minutes. At this stage, the dialyzed hemolysate was more or less salt free, but some DPG or other organic anionic effectors of hemoglobin was still attached to the hemoglobin. The DPG and anionic effectors were removed on an amberlite MB-3 column. Volumes of 100–200 ml. of hemolysate were passed over the MB-3 column, equilibrated with deionized water.

6.3. Stability of BTC Crosslinked Hemoglobin

HbA (0.413 mM) tetramers were crosslinked with 1,3 di-(3,5-dibromosalicylic) BTC (2.063 M) in 50 mM Tris, pH 8.2 for 18 hours at room temperature. The reaction products were applied to a first DEAE Sepharose column (DEAE-Sepharose Column 1) and eluted with 0–0.25 M NaCl (500 ml total).

Figure 1:
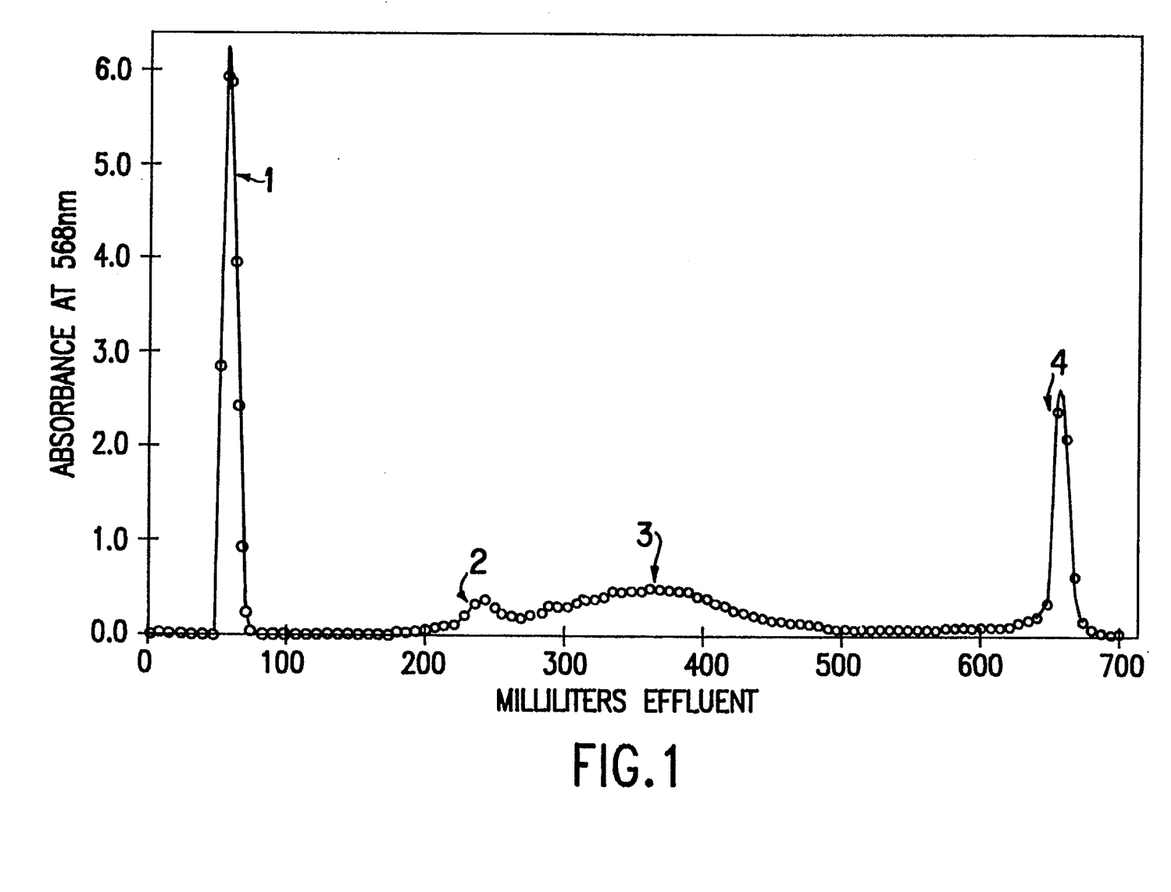
FIG. 1 shows the separation of reaction products of crosslink preparation 23 on a DEAE Sepharose column in 50 mM Tris, pH 8.0.
Figure 2:
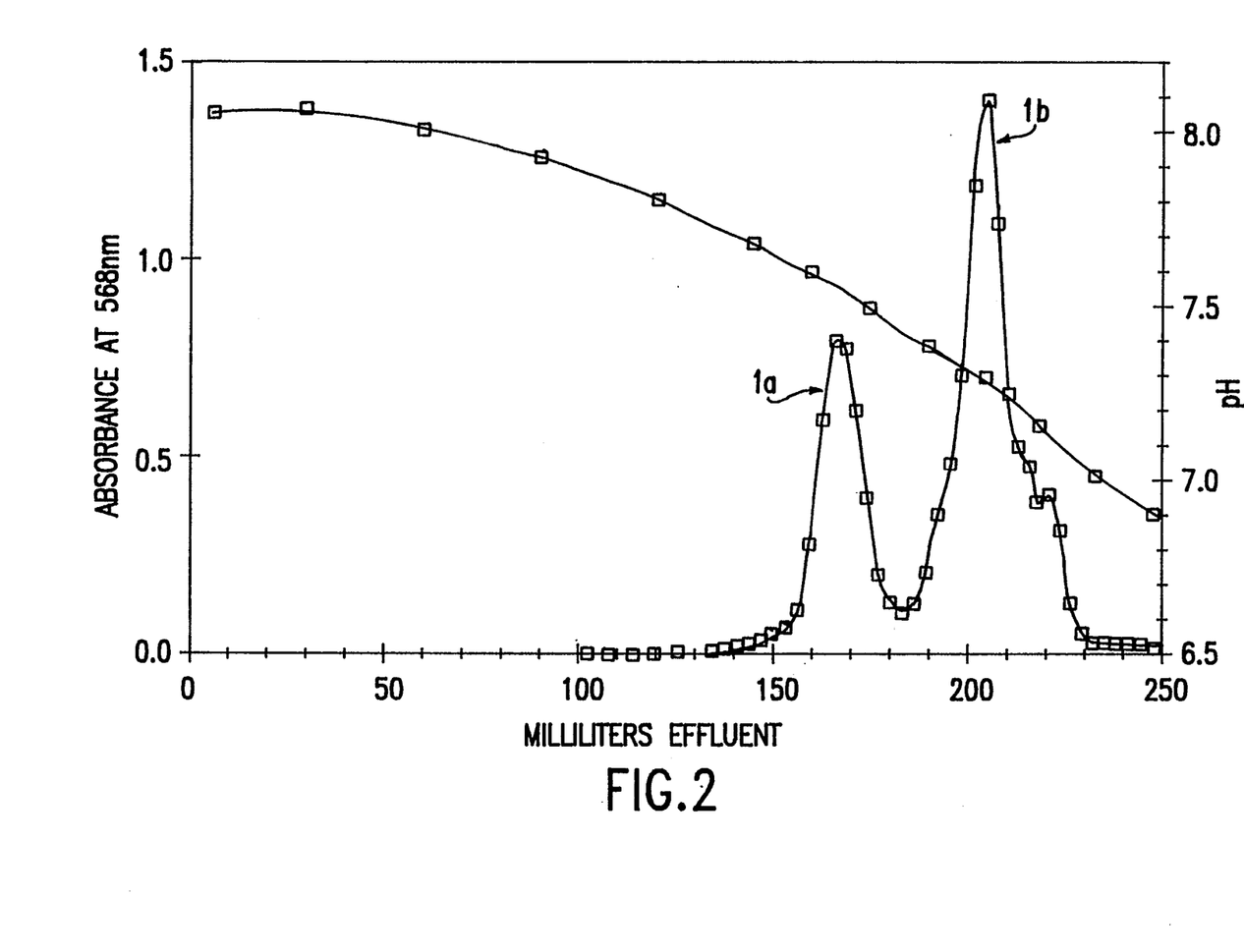
FIG. 2 shows the separation of Fraction 23-1 on a DEAE Sepharose column in 25 mM Tris, pH 8.08.
Figure 3:
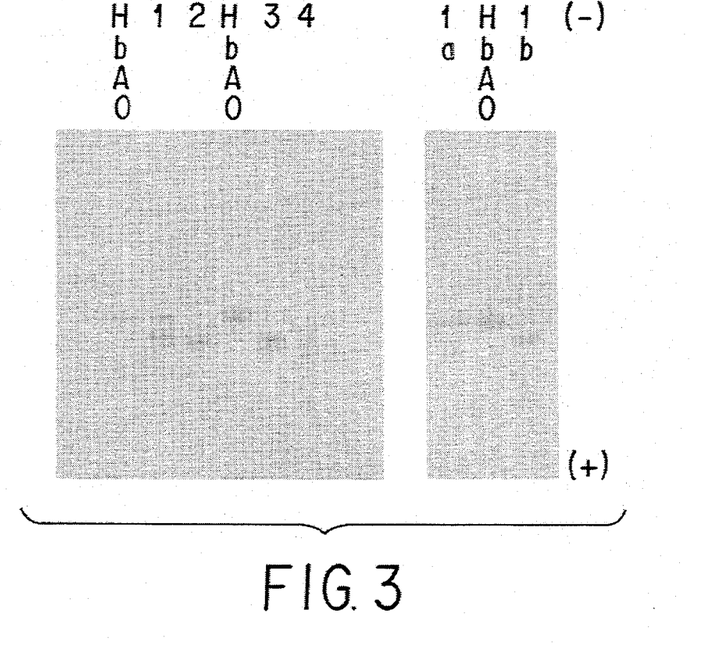
FIG. 3 shows cellulose acetate gel electrophoresis of fractions eluted from DEAE Sepharose Column 1 (left panel) and DEAE Sepharose Column 2 (right panel). Lanes 1, 2, 3, and 4 in the left panel represent fractions 1, 2, 3, and 4 respectively, and lanes 1a and 1b of the right panel represent fractions 23-1a and 23-1b. HbA$_O$ represent unmodified hemoglobin.

FIG. 1 shows the initial DEAE-Sepharose separation of the reaction products of Crosslink Prep 23 after after elution with a 0 to 0.1 M NaCl gradient. Peak 1 went into the void volume of the column while peaks 2, 3 and 4 were eluted with the gradient. The left-hand FIG. 3 shows that peak 1 is a mixture of HbA and modified hemoglobin while the other three peaks all contain modified protein. Peak 1 was further divided into two fractions by DEAE-sepharose chromatography. Peak 1a appears to be HbA while peak 1b is the modified protein component of peak 1. This is illustrated in FIG. 2 and the right-hand gel representation of FIG. 3.

Room temperature stability experiments were conducted on one fraction of Prep 23 (1b) with $HbA_O$ as a control. This study was performed by incubating the hemoglobins with and without IHP at room temperature (20°–22° C.) in 50 mM Bis-Tris, pH 7.0, 0.5 mM EDTA, and measuring the rate of methemoglobin formation by spectral analysis using established extinction coefficients at selected wavelengths for the oxy and met forms. The results are shown in Table I:

TABLE I

| EFFECT OF BTC CROSSLINKING ON HbA STABILITY | | |
|---|---|---|
| Protein | Initial Slope (−IHP) | Initial Slope (+IHP) |
| HbA | .00799 (.00558, .01039) | .02959 (.02784, .03135) |
| 23-1b | .00653 (.00437, .00869) | .00797 (.00566, .01027) |

Figure 4:
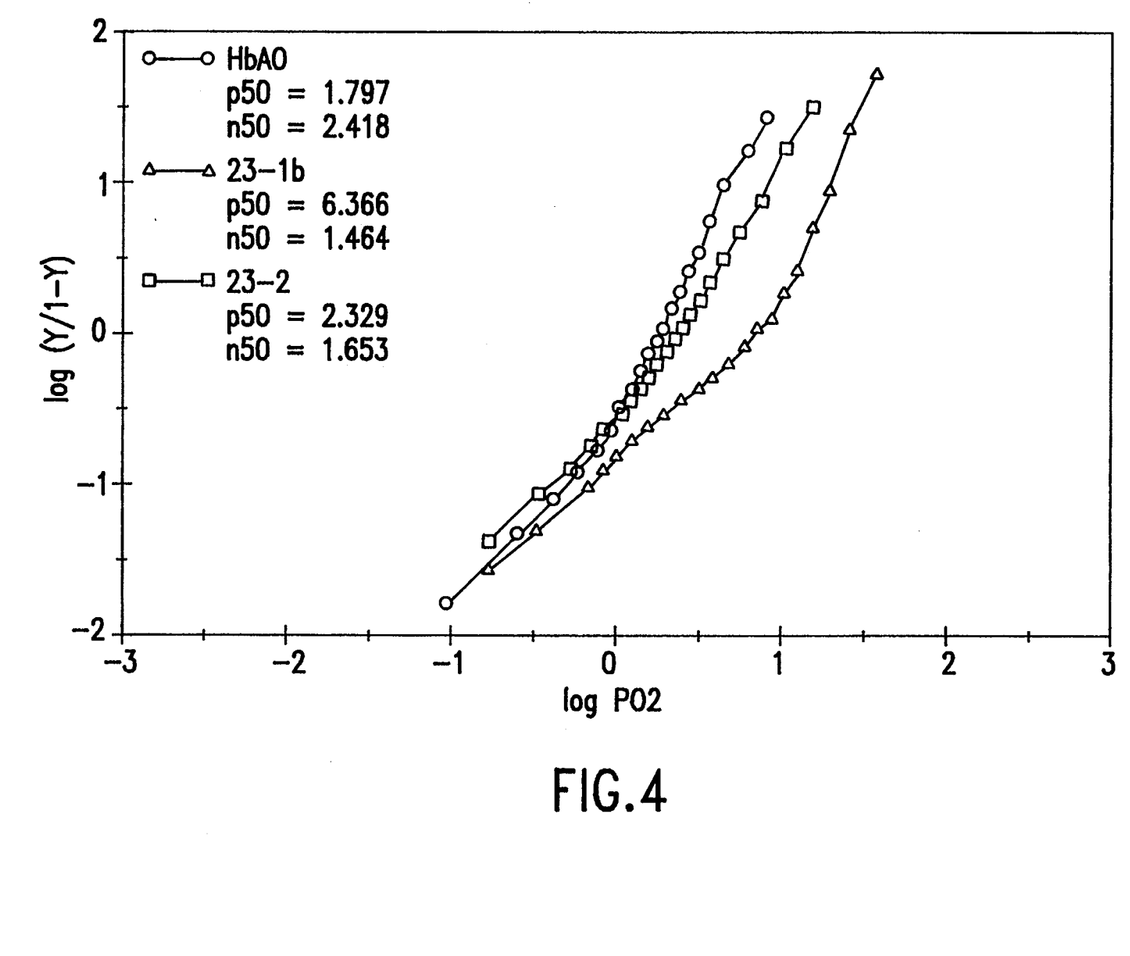
FIG. 4 shows a Hill plot of prep 23 fractions in pH 7.0 in 50 mM Bis-Tris at 20° C. in the presence and absence of IHP.
Figure 5:
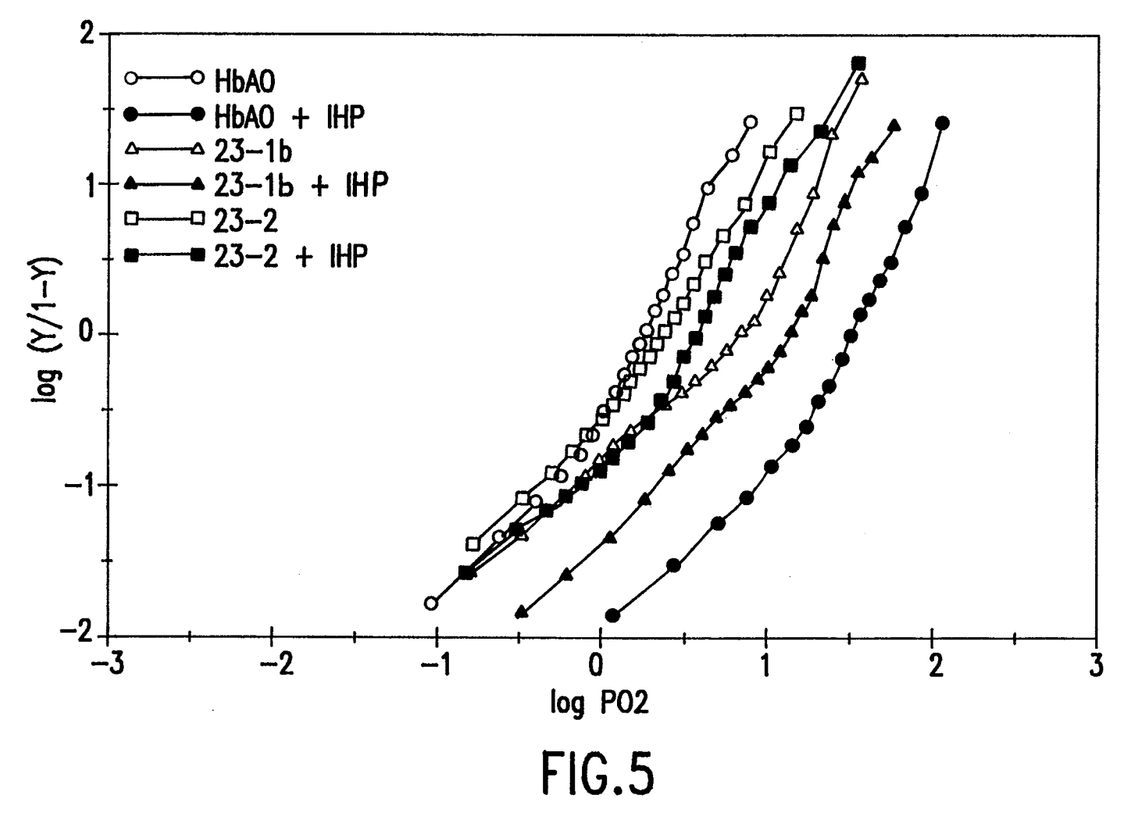
FIG. 5 shows a Hill plot of prep 23 fraction HbA$_O$, 23-1b, and 23-2 in 50 mM Bis-Tris, pH 7.0 at 20° C.

FIGS. 4 and 5 show the results of oxygen binding studies to two fractions of Prep 23 and $HbA_O$ as a control. FIG. 4 shows the three forms and their calculated $P_{50}$ values. It is evident that 23-1b has a substantially higher $P_{50}$ than does HbA, while 23-2, even though unmodified, has an oxygen affinity only slightly lower than that of the control. The results in FIG. 5 and Table I indicate that both of the modified forms are substantially less affected by the presence of IHP, suggesting that the modification to the protein blocks or hinders access to the beta-chain anion binding site.

6.4. Oxygen Equilibria Studies

For oxygen equilibrium studies, HbA (0,487 mM) tetramers were crosslinked with bis 1,3 di- (3, 5-dibromosalicylic) BTC (2.435 M) in 50 mM Bis-Tris, pH 7.8 for 15 hours at 20° C. The reaction product in 50 mM Tris, pH 7.9, hereinafter referred to as prep 18, was applied to a first DEAE Sepharose column (DEAE-Sepharose Column 1) and eluted with 0–0.25 M NaCl (500 ml total).

Figure 6:
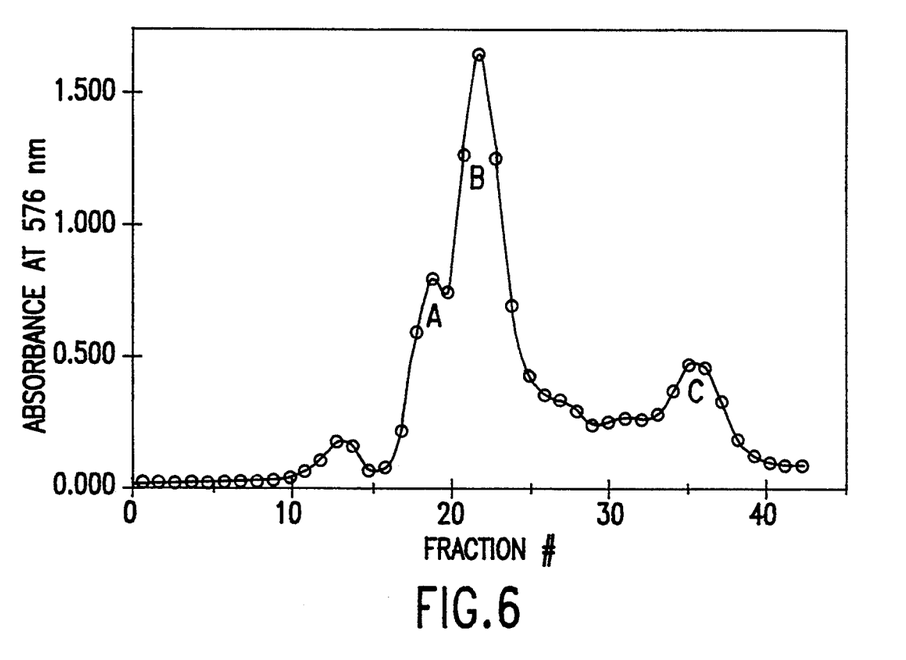
FIG. 6 shows an elution profile of preparation 18 on DEAE Sepharose column 1.

The results of DEAE—Sepharose Column 1 are shown in FIG. 6. The protein separates into four major components. Two of these components (labeled A and B) do not separate well under the conditions of this separation. The small peak which elutes earlier than Peak A (to the left of Peak A) is unmodified HbA and is discarded. The fractions which include Peaks A and B were pooled, rechromatographed, on a second DEAE Sepharose Column and eluted with a shallower, less concentrated NaCl gradient to try and gain better separation of the two fractions (0–0.125 M NaCl-1000 ml total).

Figure 7:
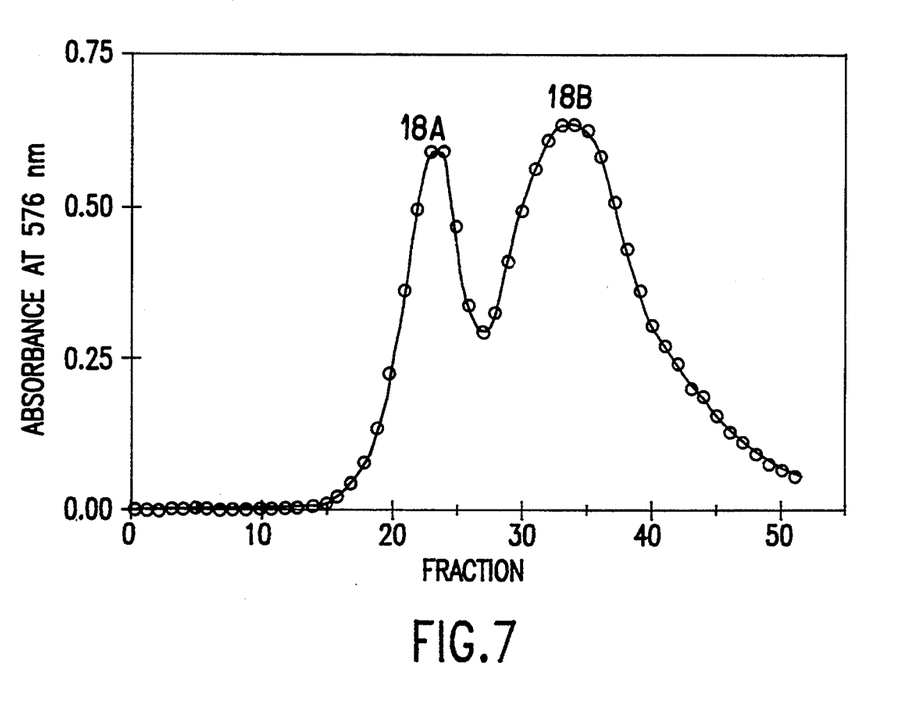
FIG. 7 shows an elution profile of preparation 18 on DEAE Sepharose column 2.

The results of the second column separation are shown in FIG. 7. Pooled fractions 19–25 were labeled 18-A. Pooled fractions 30–40 were labeled 18-B, and pooled fractions 34–38 were labeled 18-C.

Figure 8:
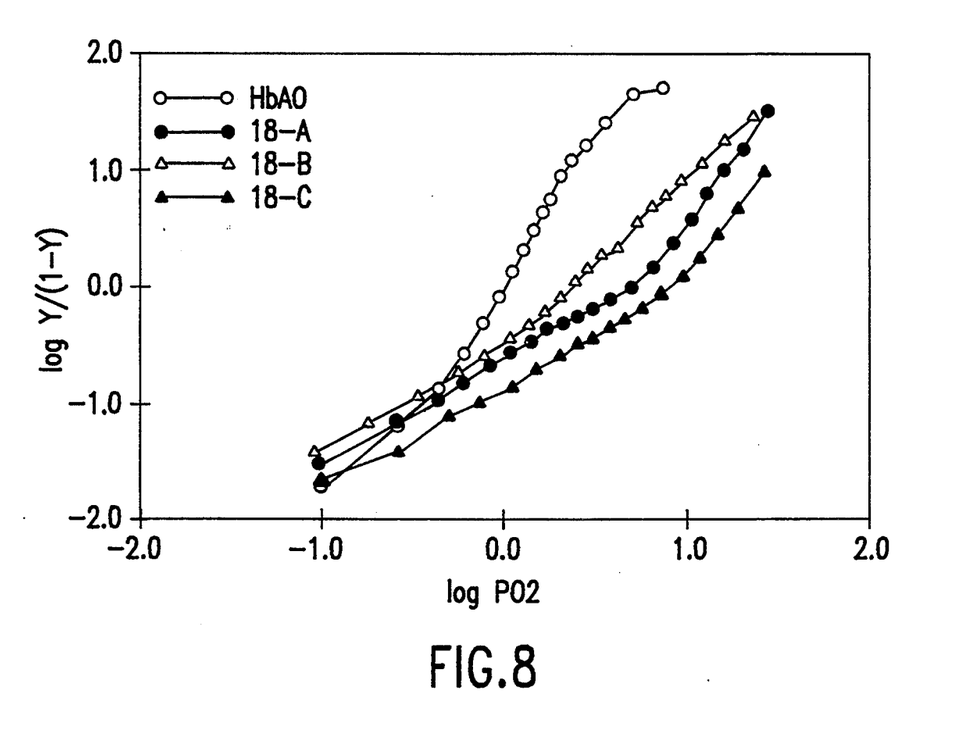
FIG. 8 shows a Hill plot of prep 23 fractions in 50 mM Bis-Tris, pH 7.0 at 20° C.

The oxygen equilibria curves for the separated fractions of Preparation 18 are shown in FIG. 8 and the results are compiled in Table II:

TABLE II

| Fraction | $N_{50}$ | $P_{50}$ |
|---|---|---|
| HbA | 2.95 | 1.006 |
| 18-A | 1.46 | 4.858 |
| 18-B | 1.65 | 2.256 |
| 18-C | 1.38 | 7.753 |

The curves for 18-A and 18-C show a biphasic type of oxygen binding curve. The $P_{50}$ values were determined by tonometry (Riggs and Wolbach, 1956, J. Gen. Physiol. 39:585–605). Specifically, a hemoglobin solution was placed in a gas-tight vessel which has an attached spectrophotometer cell. The solution was deoxygenated by a series of repeated vacuum evacuations followed by nitrogen purges. After the deoxygenated state was obtained, a "deoxy" spectrum was obtained. Next, a series of metered oxygen additions were made with a spectrum taken after each addition yielding a set of curves from which can be calculated (using established extinction coefficients) the degree of saturation of the heme sites with oxygen as a function of the oxygen partial pressure. These results indicate that that all of the crosslinked preparations have a substantially lower oxygen affinity than does $HbA_O$.

6.5. Oxygen Off Kinetics

Oxygen off kinetics were performed on the separated protein fractions both with and without inositol hexaphosphate (IHP).

The oxygen ($O_2$) off rate is the rate of dissociation of $O_2$ from oxyhemoglobin and was determined by stopped-flow spectrophotometry (Olson in Methods in Enzymology vol 76, E. Antonini, L. Rossi-Bernardi, and E. Chancone, eds., Academic Press, N.Y. (1981), pp. 438–449). Specifically, a solution of oxyhemoglobin was mixed rapidly with a solution of sodium dithionite and the absorbance of the reaction mix was monitored at a wavelength which allows the discrimination of oxyhemoglobin and deoxyhemoglobin (437.5). Sodium dithionite rapidly scavenges the free oxygen in the solution and oxygen which becomes available from the thermodynamic dissociation of oxyhemoglobin into deoxyhemoglobin and oxygen. The rate of absorbance change measured is thus proportional to the first order dissociation of oxyhemoglobin into deoxyhemoglobin and oxygen.

The oxygen "off" rates for $HbA_O$ and the three modified forms (18-A, B, and C) were fitted by standard nonlinear least squares methods to several computer generated standard models. The best fit was to a model which assumes that the data is the sum of two independent first order processes. In Table III, $k_{fast}$ is the rate constant of the faster of these processes and $k_{slow}$ is the rate constant of the slower; $p_{fast}$ is the proportion of the total absorbance change which is estimated to be due to the species which gives rise to $k_{fast}$. dA represents the total absorbance change at the monitoring wavelength (437.5 nm) for the entire process. Therefore, dA is proportional to the amount of oxygen carrier present.

The results of these studies are shown in FIG. 8 and compiled in Table III:

TABLE III

| # | Sample | dA | $P_{fast}$ | $k_{fast}$ (/sec) | $k_{slow}$ (/sec) |
|---|--------|------|-------|-------|-------|
| 1 | HbA | .6806 | .8797 | 29.19 | 6.02 |
| 2 | | .6853 | .8148 | 31.37 | 9.17 |
| 3 | | .6803 | .9111 | 27.11 | 2.84 |
| 4 | | .6779 | .9439 | 25.11 | — |
| | | .6810 | .8874 | 28.20 | 6.01 |
| | | ±.0031 | ±.0550 | ±2.69 | ±3.17 |
| 7 | 18-A | .7351 | .5988 | 85.40 | 10.66 |
| 8 | | .7289 | .5436 | 95.73 | 12.99 |
| 9 | | .7206 | .5914 | 84.93 | 10.77 |
| 10 | | .7271 | .5291 | 97.89 | 13.55 |
| | | .7279 | .5657 | 90.99 | 11.99 |
| | | ±.0060 | ±.0346 | ±6.78 | ±1.49 |
| 11 | 18-B | .7515 | .6069 | 54.38 | 8.63 |
| 12 | | .7638 | .6211 | 53.01 | 8.37 |
| 13 | | .7790 | .4694 | 64.58 | 12.98 |
| 14 | | .7619 | .4626 | 67.56 | 13.24 |
| | | .7641 | .5400 | 59.88 | 10.81 |
| | | ±.0113 | ±.0857 | ±7.27 | ±2.67 |
| 15 | 18-C | .7082 | .6343 | 74.15 | 10.48 |
| 16 | | .7305 | .6040 | 76.04 | 11.48 |
| 17 | | .7282 | .6241 | 68.63 | 10.23 |
| 18 | | .7319 | .5850 | 73.53 | 11.41 |
| | | .7247 | .6119 | 73.09 | 10.90 |
| | | ±.0111 | ±.0219 | ±3.16 | ±0.64 |
| 19 | HbA + IHP | .4339 | .5186 | 155.49 | 29.88 |
| 20 | | .4328 | .4908 | 172.51 | 31.43 |
| 21 | | .4678 | .4778 | 169.57 | 31.29 |
| 22 | | .4874 | .4946 | 150.06 | 29.68 |
| | | .4555 | .4955 | 161.91 | 30.57 |
| | | ±.0278 | ±.0170 | ±10.84 | ±0.92 |
| 23 | 18-A + IHP | .6934 | .5433 | 120.64 | 15.69 |
| 24 | | .6937 | .5629 | 116.70 | 14.80 |
| 25 | | .6940 | .6310 | 99.67 | 11.33 |
| 26 | | .6987 | .5601 | 116.82 | 14.87 |
| | | .6950 | .5743 | 113.46 | 14.17 |
| | | ±.0026 | ±0388 | ±9.37 | ±1.94 |
| 27 | 18-B + IHP | .7388 | .6180 | 63.93 | 11.62 |
| 28 | | .7464 | .6504 | 62.05 | 10.74 |
| 29 | | .7600 | .6884 | 58.81 | 8.88 |
| 30 | | .7692 | .6932 | 58.95 | 8.63 |
| | | .7536 | .6625 | 60.94 | 9.97 |
| | | ±.0136 | ±.0353 | ±2.49 | ±1.45 |
| 31 | 18-C + IHP | .7022 | .6082 | 88.24 | 13.61 |
| 32 | | .7289 | .6475 | 84.37 | 12.05 |
| | | .7536 | .6279 | 86.31 | 12.83 |
| | | ±.0189 | ±.0278 | ±2.74 | ±1.10 |

In the absence of IHP, HbA shows basically (90%) one phase with the expected "off" rate. All three cross-linked fractions show strongly biphasic curves each with two components in approximately equal proportions. (This correlates nicely with the oxygen equilibria data discussed above). When IHP was added to the samples approximately half of the HbA becomes quickly reacting while the other half stays at the original rate. This is typical of the increase in beta chain "off" rate and chain heterogeneity induced by the addition of the strong allosteric effector.

For the modified proteins, the addition of IHP induces mild increases in the fast oxygen "off" rates of 18-A and 18-C with no differences in the fast rate associated with 18-B or the slow rates associates with any of the modified proteins. It is thus apparent that the BTC crosslinker has somewhat the same effect on chain heterogeneity of the modified proteins as IHP has when added to HbA. The mild increases in oxygen "off" rates seen upon addition of IHP to 18-A and 18-C suggests that the anion binding site might still be unblocked in these forms.

The invention described and claimed herein is not to be limited in scope by the specific embodiments herein disclosed, since these embodiments are intended as illustrations of several aspects of the invention. Any equivalent embodiments are intended to be within the scope of this invention. Indeed various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What is claimed is:

1. Stroma-free tetrameric mammalian hemoglobin having an affinity for oxygen which is lower than that of non-crosslinked hemoglobin A, and which is cross-linked with a benzenetricarboxylate derivative, which derivative has at least two reactive sites capable of covalent bonding with and crosslinking of two peptide chains.

2. The stroma-free tetrameric hemoglobin according to claim 1 in which the hemoglobin is derived from a human.

3. Stroma-free tetrameric mammalian hemoglobin having an affinity for oxygen which is lower than that of non-crosslinked hemoglobin A, and which is cross-linked with bis 1,3-(3,5-dibromosalicyl)benzenetricarboxylate.

4. The stroma-free tetrameric hemoglobin according to claim 1 in which the $P_{50}$ is at least twice as high as the $P_{50}$ hemoglobin A when both of said $P_{50}$ values are measured under substantially the same conditions.

5. A method for producing stroma-free crosslinked hemoglobin having an affinity for oxygen which is lower than that of non-crosslinked hemoglobin A comprising:

(a) crosslinking hemoglobin with a benzenetricarboxylate derivative; and (b) isolating the crosslinked hemoglobin of step (a).

6. Stroma-free tetrameric mammalian hemoglobin having an affinity for oxygen which is lower than that of non-crosslinked hemoglobin A, and which is cross-linked with a crosslinking agent having the formula in which $X_1$ and $X_2$ are selected from the group consisting of H, Br, I, and $NO_2$.

7. A method for producing stroma-free crosslinked hemoglobin having an affinity for oxygen which is lower than that of non-crosslinked hemoglobin A comprising:

(a) crosslinking hemoglobin with a crosslinking agent having the formula in which $X_1$ and $X_2$ are selected from the group consisting of H, Br, I, and $NO_2$; and (b) isolating the crosslinked hemoglobin of step (a).

8. A method for producing stroma-free crosslinked hemoglobin having an affinity for oxygen which is lower than that of non-crosslinked hemoglobin A comprising;

(a) crosslinking hemoglobin with bis 1,3-(3,5-dibromosalicyl)benzenetricarboxylate; and (b) isolating the crosslinked hemoglobin of step (a).

9. The stroma-free tetrameric hemoglobin according to claims 3, 4, or 6 in which the hemoglobin is derived from a human.

* * * * *